United States Patent [19]

Wilson et al.

[11] Patent Number: 4,758,612

[45] Date of Patent: Jul. 19, 1988

[54] CEMENT-FORMING COMPOSITIONS

[75] Inventors: Alan D. Wilson, Liphook; Havard J. Prosser, Royston; David M. Groffman, Harrow; Gary S. Sayers, London, all of England

[73] Assignee: National Research Development Corporation, England

[21] Appl. No.: 921,626

[22] Filed: Oct. 21, 1986

[30] Foreign Application Priority Data

Oct. 25, 1985 [GB] United Kingdom ............... 8526367

[51] Int. Cl.$^4$ .................. A61K 6/08; C08K 3/00; C08K 5/53
[52] U.S. Cl. ........................... 524/5; 523/116; 524/2; 524/123; 524/124; 524/404
[58] Field of Search ............... 523/116, 5; 524/2, 123, 524/124, 404

[56] References Cited

U.S. PATENT DOCUMENTS

| 4,527,979 | 7/1985 | McLean et al. | 523/116 |
| 4,540,738 | 9/1985 | Zimmermann | 524/124 |
| 4,569,954 | 2/1986 | Wilson et al. | 523/116 |
| 4,585,845 | 4/1986 | Engelhardt et al. | 524/2 |

Primary Examiner—Joseph L. Schofer
Assistant Examiner—Peter D. Mulcahy
Attorney, Agent, or Firm—Jacobs & Jacobs

[57] ABSTRACT

A hardenable composition which comprises (i) a poly(-carboxylic acid) or precursor thereof (as herein defined); (ii) a particulate ion-leachable silicate, aluminosilicate or metal oxide reactable with (i) in the presence of water to set to a hardened composition; and (iii) a compound comprising at least one phosphorus-carbon or phosphorus-boron covalent bond, in an amount effective in service to extend the working time of the composition.

28 Claims, No Drawings

CEMENT-FORMING COMPOSITIONS

This invention relates to cement-forming compositions; more particularly, this invention relates to ionomeric cement-forming compositions with improved setting characteristics, and to hardened cementitious masses formed therefrom.

In GB No. 1139430 there is disclosed a process for the preparation of a surgical cement which comprises mixing a sugically acceptable grade of zinc oxide powder with an aqueous solution containing at least 40% by weight of a polyacrylic acid having a viscosity determined average molecular weight of 15,000 to 150,000 in a powder to liquid ratio of between 0.5:1 to 4:1 by weight to give a mass that remains plastic long enough to be formed with a desired shape prior to hardening as a surgical cement.

In GB No. 1316129 there is disclosed a process for the preparation of a surgical cement which comprises mixing a fluoroaluminate glass powder wherein the ratio by weight of silica to alumina is from 1.5 to 2.0 and the ratio by weight of flourine to alumina is from 0.6 to 2.5, or wherein the ratio by weight of silica to alumina is from 0.5 to 1.5 and the ratio by weight of flourine to alumina is from 0.25 to 2.0 with a surgically acceptable water soluble poly(carboxylic acid) having a relative viscosity of from 1.05 to 2.00 centipoise in the presence of water, to give a mass that remains plastic long enough to be formed into a desired shape prior to hardening as a surgical cement.

GB No. 1422337 discloses a process for the production of a poly(carboxylate) cement which comprises mixing a water soluble poly(carboxylic acid) having a relative viscosity of from 1.05 to 2.00 with a cement powder in the presence of a water soluble chelating agent and water to give a plastic mass which rapidly hardens to form a poly(carboxylate) cement.

This invention seeks to provide ionomeric cement-forming compositions in which the setting characteristics are improved in certain respects.

According, therefore, to one aspect of this invention, there is provided a hardenable composition which comprises (i) a poly(carboxylic acid) or precursor thereof (as herein defined); (ii) a particulate ion-leachable silicate, aluminosilicate or metal oxide reactable with (i) in the presence of water to set to a hardened composition; and (iii) a compound comprising at least one phosphorus-carbon or phosphorus-boron covalent bond, for example phosphonic acid group, or a salt thereof, in an amount effective in service to extend the working time of the composition.

The preferred poly(carboxylic acid)s suitable for use as (i) are those prepared by the homopolymerisation and copolymerisation of unsaturated aliphatic carboxylic acids for example aconitic acid, acrylic acid, citraconic acid, fumaric acid, glutaconic acid, itaconic acid, maleic acid, mesaconic acid, methacrylic acid, and tiglic acid; and the copolymerisation of these acids with other unsaturated aliphatic monomers for example vinyl monomers, such as vinyl hydrocarbon monomers, vinyl ethers, acrylamide or acrylonitrile. Particularly preferred are the homopolymers of acrylic acid and its copolymers with one or more of aconitic, fumaric, itaconic, maleic, mesaconic, methacrylic, muconic or tiglic acid, particularly copolymers of acrylic acid and itaconic acid. Especially preferred are homopolymers of acrylic acid. Good results have also been obtained using copolymers of vinyl methyl ether and maleic acid and those described and claimed in our GB No. 1484454.

It is also possible to use a precursor of a poly(carboxylic acid) as (i); as used in this specification, "precursor" means a polymer which will be transformed into the poly(carboxylic acid) on hydrolysis, for example a poly(carboxylic acid anhydride); furthermore, polyacrylic acids may be prepared by hydrolysis of corresponding polyacrylonitriles. The precursor of a poly(carboxylic acid) may be a homopolymer of an unsaturated carboxylic acid anhydride or a copolymer with an above mentioned other carboxylic acid or anhydride thereof; or a copolymer of an unsaturated carboxylic acid anhydride with an unsaturated aliphatic monomer, for example vinyl monomers, such as vinyl hydrocarbon monomers, vinyl ethers, acrylamide or acrylonitrile. Good results may be obtained by using homopolymers of maleic anhydride or vinyl orthophthalic anhydride, or copolymers thereof, especially block copolymers thereof, with ethylene, propylene, butenes, styrene and vinyl methyl ether.

The poly(carboxylic acid) or precursor thereof is preferably linear, although branched polymers may also be used. Preferably, the polymer has an average molecular weight from 1,000 to 1,000,000, more preferably from 1,000 to 250,000, and most preferably from 10,000 to 25,000. In this specification the average molecular weight is defined as being that measured by ultracentrifuging.

The particulate, ion-leachable component (ii) may comprise a basic metal oxide which may have been deactivated by heat treatment; for example, zinc oxide to which there may be added up to about 10% by weight of another metal oxide such as magnesium oxide. Alternatively, or in addition thereto, component (ii) may comprise a silicate or an aluminosilicate. The silicate may also be a naturally-occurring orthosilicate, pyrosilicate, cyclic or chain silicate comprising recurring metasilicate units, or aluminosilicate having an Al:Si molar ratio greater than 2:3; or blast furnace slags; or Portland cement. Examples of such materials include aphrosiderite, danalite, gehlenite, hemimorphite, larnite, levynite, nepheline, muscovite, sodalite, scolecite, spurrite, thuringite, willemite, wollastonite, (including calcined wollastonite).

The preferred particular ion-leachable silicates or (fluoro) aluminosilicates (ii) are glasses wherein the ratio by weight of acidic to basic oxides in the glass is such that the glass will react with (i) in the presence of water to set to a hardened composition. By "(fluoro)aluminosilicate" is meant herein fluoroaluminosilicate or aluminosilicate. The principal acidic oxide in the aluminosilicate glass is a silica, although the glass may also contain minor amounts of other anhydrides such as phosphorus pentoxide and boric oxide. The principal basic oxide in the glass is alumina which, although it has amphoteric properties, can be considered for the purposes of the present invention solely as a basic oxide. Particularly preferred aluminosilicate glasses fall within the composition range of 10 to 65% w/w silica and 15 to 50% w/w alumina.

The aluminosilicate glass desirably contains at least one other basic oxide, preferably calcium oxide, which may be present in the glass composition in an amount from 0 to 50% w/w. The calcium oxide may be partly or wholly replaced by sodium oxide or other basic oxide such as strontium oxide or barium oxide or a mixture of basic oxides, although in some applications the presence of sodium oxide may be undesirable as this oxide tends to increase the solubility of the resulting cement. Preferred glasses for use in the present invention containing alumina, silica and calcium oxide are the gehlenite and anorthite glasses, and in general glasses falling within the composition range 10 to 65% w/w silica, 15 to 50% w/w alumina and 0 to 50% w/w calcium oxide.

Other aluminosilicate glasses suitable for use in the present invention may contain fluoride, suitably up to 15% by weight preferably less than 10% by weight. A class of fluoroaluminosilicate glasses particularly suited to dental applications are those wherein the ratio by weight of silica to alumina is from 1.5 to 2.0 and the ratio by weight of silica to alumina is from 0.5 to 1.5 and the ratio by weight of fluorine to alumina is from 0.25 to 2.0.

Particularly preferred glasses are those wherein the glass has a composition within the following systems:
(a) $CaO$—$Al_2O_3$—$SiO_2$;
(b) $CaO$—$Al_2O_3$—$SiO_2$—$CaF_2$;
(c) $CaF_2$—$Al_2O_3$—$SiO_2$;
(d) $CaF_2$—$Al_2O_3$—$SiO_2$—$AlPO_4$; or
(e) $CaF_2$—$Al_2O_3$—$SiO_2$—$AlPO_4$—$AlF_3$—$Na_3AlF_6$.

The aluminosilicate glasses suitable for use in the present invention may be prepared by fusing mixtures of the components in the appropriate proportions at temperatures above 900° C. and preferably in the range of 1050° C. to 1600° C. The mixture is preferably fused from 1 to 4 hours. Silica and alumina may be included in the mixture as oxides, though it is convenient to add calcium oxide and sodium oxide as calcium carbonate and sodium carbonate respectively, and reference to the presence of these oxides in a glass fusion mixture includes the possibilities that they may be added as carbonates or as other compounds which decompose similarly under glass fusion conditions to give the oxides.

The addition of carbonates to the fusion mixture lowers the fusion temperature and thus these can be considered as fluxing agents. If desired, however, the mixture may contain an additional fluxing agent, and this has been found to be important with glass compositions containing less than 10% w/w of calcium oxide. In this connection, fluorides such as fluorite and cryolite have been found to be especially useful as fluxing agents, although it is desirable not to use large amounts of fluorides in the fusion mixture. Other fluxing agents, for example calcium phosphate and aluminium phosphate may also be used. The total amount of fluxing agents present in the mixture, including carbonates, may be up to 50% by weight, based on the total weight of mixture.

After fusion the glass may be poured off and cooled rapidly, for example, in air or water or some combination of both. To the first approximation the proportions of the same element are present as in the mixture. Some fluorine may, however, be lost from the fluoride fluxing agent during the reaction.

Glasses used in the present invention may be readily obtained in fine powder form. The degree of fineness of the power should preferably be such that it produces a smooth cement paste which sets within an acceptable period when mixed with the poly(carboxylic acid) in the presence of water. Preferably the degree of fineness of the powder is such that is will pass through a 150 mesh B.S. sieve and most preferably such that it will pass through a 350 B.S. sieve. Mixtures of different glasses may be used if desired. Preferred are (fluoro)aluminosilicate glass powders.

Component (iii) of the hardenable composition of this invention comprises a compound comprising at least one phosphorus-carbon or phosphorus-boron covalent bond, for example a phosphonic acid group, or a salt thereof, in an amount effective in service to extend the working time of the composition. Preferably, the component (iii) comprises a polybasic phosphonic acid including a diabasic phosphonic acid. Particularly effective such compounds also comprise at least one other complexing group, suitably a hydroxy or an amino, preferably a tertiary amino, group. It has been found that the materials sold under the trade mark "DEQUEST" ("DEQUEST" is a registered trade mark) are very suitable as component (iii), especially:

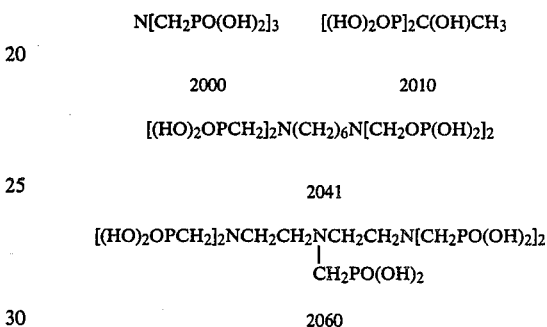

It is particularly desirable that component (iii) is soluble in, and preferably completely miscible in, an aqueous solution of (i).

In accordance with a further aspect of this invention, there is provided a hardenable composition as aforesaid which further comprises a complexing agent soluble in an aqueous solution of (i). The complexing agent may comprise a fluoride ligand or, more preferably, a chelating agent. The chelating agent may comprise a plurality of carboxyl groups, for example aconitic, itaconic, maleic, mellitic or tricarballylic acid; it may also comprise at least one hydroxyl group. Particularly preferred such chelating agents comprise citric malic or tartaric acid. A further suitable type of chelating agent comprises a multivalent metal chelate, the metal of which may suitably be the same as that in (iii), for example a beta-diketone chelate, such as is formed by aluminium or chromium, or an EDTA chelate, such as is formed by copper or zinc.

Such chelating agents are suitable present in an amount up to 20% by weight, preferably 0.1% to 10% by weight, especially 3% to 8% by weight, based on the weight of (i).

Suitably (iii) is present in an amount of up to 20% by weight, preferably 1% to 10% by weight, based on the weight of (i).

In accordance with a further aspect of this invention, there is provided a mixture suitable for use in preparing a hardenable composition as aforesaid, which mixture comprises a compound (iii) and (a) a complexing agent or (b) a poly(carboxylic acid) or precursor thereof (i) or (c) a particulate ion-leachable silicate (fluoro)aluminosilicate or metal oxide (ii), all as herein defined. Preferably, the mixture comprises a compound (iii) and both (a) and (b) or both (a) and (c), especially an aqueous mixture.

The hardenable composition of the invention may be supplied or stored in any suitable manner providing that means are provided to present reaction of the ion-leachable particulate material (ii) with the poly(carboxylic acid) (i) in the presence of water. Thus, the composition may be supplied or stored as a dry mixture, suitably comprising an intimate powder, of the poly(carboxylic acid) or precursor thereof (i) in particulate form; particulate ion-leachable silicate or (fluoro)aluminosilicate (ii); and compound (iii). When the latter is in powder form, it preferably has a degree of fineness such that it will pass through a 150 B.S. mesh sieve.

It is also possible to supply or store the composition as a two-component pack, one of which pack components may comprise an aqueous medium; indeed it may simply comprise distilled water, optionally tinted. In many cases, however, it is found that mixing, and the physical properties of the resulting cement, are improved by providing the poly(carboxylic acid) or compound (iii) or complexing agent, all as herein defined, as an aqueous solution which may suitably comprise a mixture as hereinabove defined of such constitutents. Such aqueous solutions may contain from 20 to 65% by weight of the poly(carboxylic acid). Where the compound (iii) is also included in that solution it must be free from any tendency to precipitate the poly(carboxylic acid) (i). It may instead be included in admixture with the particulate ion-leachable silicate or (fluoro)aluminosilicate (ii) or indeed in both. It may be found convenient to include the compound (iii) in an aqueous solution while the poly(carboxylic acid) or precursor thereof (i) is in dry admixture with the particulate ion-leachable silicate or (fluoro)aluminosilicate (ii). Furthermore, any chelating agent present may be included either with the particulate ion-leachable silicate or (fluoro)aluminosilicate (ii) or in an aqueous phase.

In addition, hardenable compositions according to the present invention may comprise an amount of filler, suitably from 10 to 65%, preferably 25 to 50%, by weight of filler of the total weight of the components. Such materials include sand, talc, and fibrous materials such as asbestos and nylon. Inclusion of an inert filler is found to minimise any problem of contraction and cracking of the hardened composition which may occur.

Furthermore, where the hardened composition is intended for use in a low humidity environment it is found beneficial to incorporate, in the hardenable composition, an amount, suitably from 5 to 70% by weight, of an emulsion of a substantially water-insoluble polymer, particularly a polymer comprising carboxyl groups capable of participating in the setting reaction to form the hardened composition. Examples of such water-insoluble polymers include copolymers of unsaturated aliphatic carboxylic acids, such as acrylic acid, methacrylic acid or itaconic acid, with unsaturated aliphatic esters, such as methyl methacrylate, ethyl methacrylate and ethyl acrylate.

The hardenable compositions of this invention may be used as dental cements and have many application in dentistry including use as filling materials for restoring teeth and for cementing inlays and crowns into place in the tooth; as luting compositions to provide a base and/or lining in a tooth cavity or a temporary fixing for the bonds of orthodontic appliances to the teeth; and as compositions for sealing root canals after endodontic treatment. They may also be formed as hardenable sheet materials, for example by depositing the components optionally in intimate admixture, upon a flexible support web which may be woven, laid down as a non-woven fabric, cast or extruded. Preferably such a flexible support web may be a cotton bandage fabric, for example of leno weave. Such sheet materials have important surgical applications such as splinting materials.

In accordance with a still further aspect of this invention, there is provided a process for preparing a poly(carboxylate) cement which comprises mixing water, a poly(carboxylic acid) or precursor thereof (i), and a particulate ion-leachable silicate, (fluoro)aluminosilicate or metal oxide with a compound (iii), all as herein defined, especially wherein the mixture further comprises a complexing agent as herein defined.

This invention also provides a hardened mass of a poly(carboxylate) cement prepared by the aforesaid process.

The use of compounds (iii) as aforesaid is found to increase the working times of the hardenable composition, usually without increase in setting rate, even when the component (ii) comprises a metal oxide, such as zinc oxide.

In the following Examples, setting times were measured in accordance with B.S. 6039:1981 whereby a sample of the mixed cement was placed into a metal mould and 2 minutes after the start of mixing the whole assembly was placed in a humidifier, maintained at 37° C. and with a relative humidity of at least 90%. An indentor weighting 400 grams and with a tip of 1 mm diameter was placed on the cement surface for 5 seconds at a time until the needle failed to make a complete circular indentation.

All results were done in duplicate and reported to the nearest 10 seconds. Working times were measured by placing a sample of the mixed cement between the plates of a Wilson oscillating rheometer. The working time was defined by taking note of the chart recorder trace when the sweep was 95% of the full sweep, started at the commencement of mixing. Two traces were done for each powder/liquid combination and the results are reported to the nearest 10 seconds. The setting rate was determined from the trace drawn out by the Wilson oscillating rheometer whilst the cement is setting. The setting rate was defined by the slope of the line drawn at a tangent to the envelope of the trace. For compressive strength measurements cements were mixed and packed into split moulds 6 mm high and internal diameter 4 mms. The mounds were filled, clamped up and placed into an incubator at 37° C., 3 minutes after the start of mixing. The cement pellets were removed 1 hour after the start of mixing, the ends were ground plane and then placed into demineralised water at 37° C. for 23 hours. At the end of this time they were crushed in an electromechanical tester. Five specimens were tested and the standard derivation was quoted for each set.

The following Examples illustrate the invention.

EXAMPLE 1

An aluminosilicate glass powder ($SiO_2$ 25.09 wt%; $Al_2O_3$ 37.45%; $CaF_2$ 37.45% and prepared by fusing the components at 1300° C.; quenching in water at ambient temperature; and grinding to <45 μ was mixed by spatulation on a glass block at a powder:liquid ratio of 3:1 g/ml with aqueous solutions of the composition shown in Table 1. The working times, setting times and setting rates, determined as aforesaid are shown in Table 1.

TABLE 1

| Composition (w/w %) of aqueous solution | | Working time (min) at 23° C. | Setting time (min) at 37° C. | Setting rate (min$^{-1}$) at 23° C. |
|---|---|---|---|---|
| Polyacid[1] | additive[2] | | | |
| 50 | 0 | 1.5 | 6.5 | 55.8 |
| 42 | 8 | 2.7 | 8.7 | 42.8 |
| 40 | 10 | 3.0 | 6.75 | 63.9 |
| 39.75 | 10.25 | 0.6 | 1.1 | 100 |

[1]poly(acrylic acid): VERSICOL E7 (average molecular weight 30,000) ex Allied Colloids Ltd.
[2]DEQUEST 2000 ex Monsanto Ltd.

It will be seen that the additive is effective to increase both the working time (which is doubled) and setting rate of the setting glass ionomer cement provided that the concentration of additive is kept below a critical level. It is believed, though not ascertained, that above this critical level, when making and setting times are drastically reduced, a competing phosphonate cement-forming reaction sets in.

EXAMPLES 2 AND 3

Example 1 was repeated with the glass powder replaced by zinc oxide powder. Results are shown in Table 2.

TABLE 2

| Example | Powder | Composition (w/w %) aqueous solution | | Working time (min) at 23° C. | Setting time (min) at 37° C. | Setting rate (min$^{-1}$) at 23° C. |
|---|---|---|---|---|---|---|
| | | polyacid[2] | additive | | | |
| 2 | Poly F[1] | 50 | 0 | 1.3 | 4.4 | 59.8 |
| 2 | " | 45 | 5[3] | 2.0 | 5.5 | 48.0 |
| 2 | " | 45 | 5[4] | 2.1 | 6.5 | 38.1 |
| 2 | " | 45 | 5[5] | 1.2 | 5.0 | 44.0 |
| 3 | Poly F plus 6 | 50 | 0 | 3.5 | 11.5 | 16.9 |
| 3 | " | 42 | 8[3] | 11.0 | 31.0 | 13.3 |
| 3 | " | 40 | 10[3] | 13.0 | 26.5 | 15.0 |
| 3 | " | 45 | 5[4] | 7.0 | 18.5 | 17.6 |
| 3 | " | 45 | 5[5] | 3.1 | 12.5 | 14.2 |

[1]deactivated zinc oxide powder ex Dentsply Ltd.
[6]deactivated zinc oxide powder ex Dentsply Ltd. blended with solid polyacid to form, on admixture, a solution as shown in Column 2.
[2]Poly(acrylic acid) as used in Example 1
[3]DEQUEST 2000 ex Monsanto Ltd.
[4]DEQUEST 2010 ex Monsanto Ltd.
[5]tartaric acid (comparative runs)

It will be seen that the additive is effective, unlike tartaric acid, to increase both the working time and the setting time of the setting zinc poly(carboxylate) cement.

EXAMPLE 4

An aluminosilicate glass powder (SiO$_2$ 28.97 wt %; Al$_2$O$_3$ 16.56%; Na$_3$ AlF$_6$ 4.97%; AlPO$_4$ 9.93%; CaF$_2$ 34.27%; AlF$_3$ 5.30%; and prepared by fusing the components at 1150° C.; quenching in water at ambient temperature; and grinding to <45 μ was mixed by spatulation on a glass block at a power:liquid ratio of 3:1 g/ml with aqueous solutions of the composition shown in Table 3. The working times, setting times and setting rates, determined as aforesaid are shown in Table 3.

TABLE 3

| Composition (w/w %) of aqueous solution | | Working time (min, sec) at 23° C. | Setting time (min, sec) at 37° C. | Setting rate (min$^{-1}$) at 23° C. |
|---|---|---|---|---|
| Polyacid[1] | additive[2] | | | |
| 50 | 0 | 1,40 | 6 | 20 |
| 48.75 | 1.25[2] | 2,10 | 7 | 20 |
| 45 | 5[2] | 1,50 | 7 | 10 |
| 42.5 | 7.5[2] | 1,10 | 8,20 | 10 |
| 40 | 10[2] | 1 | 9,30 | 10 |
| 39 | 11[2] | 1 | 9,10 | 4 |
| 48.75 | 1.25[3] | 2,10 | 7,20 | 25 |
| 45 | 5[3] | 1,50 | 7,10 | 15 |
| 42.5 | 7.5 | <1 | 8,10 | — |
| 40 | 10[3] | <1 | 9 | — |
| 39 | 11[3] | <1 | 9 | — |
| 48.75 | 1,25[4] | 2 | 5,50 | 20 |
| 45 | 5[4] | 2,10 | 7 | 15 |
| 40 | 10[4] | 1,30 | 8 | 15 |

[1]poly(acrylic acid): VERSICOL E7 (average molecular weight 30,000) ex Allied Colloids Ltd.
[2]DEQUEST 2000 ex Monsanto Ltd.
[3]DEQUEST 2010 ex Monsanto Ltd.
[4]DEQUEST 2060 ex Monsanto Ltd.

EXAMPLE 5

Example 4 was repeated with the glass powder replaced by one of the compositions. SiO$_2$ 38.72 wt %; Al$_2$O$_3$ 22.12%; AlPO$_4$ 13.27%; CaF$_2$ 25.88% and prepared by fusing the components at 1150° C.; quenching in water at ambient temperature: and grinding to <45 μ. Results are shown in Table 4.

TABLE 4

| Composition (w/w %) aqueous solution | | Working time (min) at 23° C. | Setting time (min) at 37° C. | Setting rate (min$^{-1}$) at 23° C. | Compressive strength | |
|---|---|---|---|---|---|---|
| polyacid[1] | additive | | | | (MPa) | (SD) |
| 40 | 0 | 1,10 | 5 | 50 | | |
| 50 | 0 | 1 | 4,20 | 50 | 121 | (21) |
| 48.75 | 1.25[2] | 1,20 | 4,20 | 70 | | |
| 45 | 5[2] | 1,30 | 4,30 | 30 | 132 | (14) |
| 42.5 | 7.5[2] | 1,20 | 5,10 | 45 | | |
| 40 | 10[2] | 1 | 5 | 40 | | |
| 39 | 11[2] | 1 | 4,40 | 35 | | |
| 35 | 15[2] | <1 | 5,30 | 25 | | |
| 48.75 | 1.25[3] | 1.20 | 4;20 | 70 | | |
| 45 | 5[3] | 1,30 | 4,20 | 50 | 123 | (13) |
| 42.5 | 7.5[3] | 1 | 4,50 | 40 | | |
| 40 | 10[3] | <1 | 5,10 | 35 | | |

TABLE 4-continued

| Composition (w/w %) aqueous solution | | Working time (min) at 23° C. | Setting time (min) at 37° C. | Setting rate (min$^{-1}$) at 23° C. | Compressive strength | |
|---|---|---|---|---|---|---|
| polyacid[1] | additive | | | | (MPa) | (SD) |
| 39 | 11[3] | <1 | 4,20 | 30 | | |
| 48.75 | 1.25[4] | 1,10 | 3,50 | 45 | 151 | (10) |
| 45 | 5[4] | 1,20 | 4 | 50 | | |
| 40 | 10[4] | 1,10 | 3,50 | 45 | | |

EXAMPLE 6

Example 5 was repeated with the glass powder replaced by one of the Composition SiO$_2$ 31.38 wt %; Al$_2$O$_3$ 26.67%; CaF$_2$ 36.72%; CaCO$_3$ 5.23% and prepared by fusing the components at 1250° C.; quenching in water at ambient temperature; and grinding to <45 μ. Results are shown in Table 5.

TABLE 5

| Composition (w/w %) aqueous solution | | Working time (min) at 23° C. | Setting time (min) at 37° C. | Setting rate (min$^{-1}$) at 23° C. | Compressive strength | |
|---|---|---|---|---|---|---|
| polyacid[1] | additive | | | | (MPa) | (SD) |
| 40 | 0 | 1 | 3,20 | 60 | | |
| 50 | 0 | 1,10 | 2,30 | 120 | | |
| 48.75 | 1.25[2] | 1,10 | 3 | 130 | | |
| 48 | 2[2] | 1,10 | 3 | 65 | | |
| 45 | 5[2] | 1,30 | 2,50 | 95 | 163 | (4.2) |
| 42.5 | 7.5[2] | 1,30 | 2,50 | 80 | | |
| 40 | 10[2] | 1,40 | 3 | 95 | 180 | (8.0) |
| 39 | 11[2] | 1,40 | 2,50 | 70 | | |
| 35 | 15[2] | 1,30 | 3,20 | 75 | | |
| 48.75 | 1.25[3] | 1,10 | 2,20 | 95 | | |
| 45 | 5[3] | 1,30 | 3,10 | 90 | 116 | (30) |
| 42.5 | 7.5[3] | 1,30 | 3,20 | 70 | 138 | (19) |
| 40 | 10[3] | 1,30 | 3,20 | 85 | | |
| 39 | 11[3] | 1,30 | 3,10 | 85 | | |
| 48.75 | 1.25[4] | 1 | 3 | 85 | | |
| 45 | 5[4] | 1,10 | 2,50 | 85 | 145 | (9) |
| 40 | 10[4] | 1,20 | 3 | 100 | 138 | (17) |

EXAMPLE 7

Example 6 was repeated with the glass powder replaced by one of the composition SiO$_2$ 26.44%; Al$_2$O$_3$ 31.00%; CaCO$_3$ 42.55% and prepared by fusing the components at 1430° C.; quenching in water at ambient temperature; and grinding to <34 μ. Results are shown in Table 6.

TABLE 6

| Composition (w/w %) aqueous solution | | Working time (min) at 23° C. | Setting time (min) at 37° C. | Setting rate (min$^{-1}$) at 23° C. | Compressive strength | |
|---|---|---|---|---|---|---|
| polyacid[1] | additive | | | | (MPa) | (SD) |
| 40 | 0 | 0,50 | 3 | 145 | | |
| 50 | 0 | unable to be mixed | | | | |
| 49.5 | 0.5[2] | 1,0 | 3,20 | 40 | | |
| 49 | 1[2] | 2,10 | 5,40 | 15 | | |
| 48.75 | 1.25[2] | 2,30 | 7 | 3 | 63 | (10) |
| 48 | 2[2] | 3,40 | >2 hours | 1 | | |
| 45 | 5[2] | 1,40 | >2 hours | 4 | | |
| 42.5 | 7.5 | 1,30 | >2 hours | 4 | | |
| 40 | 10[2] | 1 | >2 hours | 8 | | |
| 39 | 11[2] | 1 | >2 hours | 8 | | |
| 48.75 | 1.25[3] | 1 | 2,50 | 110 | | |
| 45 | 5[3] | 2,10 | 5,40 | 15 | 85 | (7.6) |
| 42.5 | 7.5[3] | 2,10 | 7,20 | 4 | | |
| 40 | 10[3] | 2 | ~15 | 7 | | |
| 39 | 11[3] | 2 | ~20 | 4 | | |
| 48.75 | 1.25[4] | 1,40 | 6,10 | 20 | 95 | (19) |
| 45 | 5[4] | 3,30 | >2 hours | 2 | | |
| 40 | 10[4] | 1,40 | ~3 hours | 4 | | |

EXAMPLE 8

Example 7 was repeated with the glass powder replaced by that used in Example 1. Results are shown in Table 7.

TABLE 7

| Composition (w/w %) aqueous solution | | Working time (min) at 23° C. | Setting time (min) at 37° C. | Setting rate (min$^{-1}$) at 23° C. | Compressive strength | |
|---|---|---|---|---|---|---|
| polyacid[1] | additive | | | | (MPa) | (SD) |
| 40 | 0 | 1,10 | 3 | 65 | | |
| 50 | 0 | 1,10 | 3,30 | 65 | 125 | (13) |

TABLE 7-continued

| Composition (w/w %) aqueous solution | | Working time (min) | Setting time (min) | Setting rate (min$^{-1}$) | Compressive strength | |
|---|---|---|---|---|---|---|
| polyacid[1] | additive | at 23° C. | at 37° C. | at 23° C. | (MPa) | (SD) |
| 48.75 | 1.25[2] | 1,20 | 3,30 | 90 | | |
| 48 | 2[2] | 1,40 | 3,30 | 55 | | |
| 45 | 5[2] | 2 | 3,40 | 55 | 137 | (6.1) |
| 42.5 | 7.5[2] | 2 | 3,30 | 45 | | |
| 40 | 10[2] | 1,50 | 3,50 | 50 | 119 | (17) |
| 39 | 11[2] | 1,20 | 3,30 | 45 | | |
| 35 | 15[2] | <1 | 3,50 | 35 | | |
| 48.75 | 1.25[3] | 1,30 | 3,30 | 90 | | |
| 45 | 5[3] | 1,50 | 4 | 85 | 119 | (25) |
| 42.5 | 7.5[3] | 1,40 | 3,30 | 50 | | |
| 40 | 10[3] | 1,30 | 4 | 35 | | |
| 39 | 11[3] | <1 | 4,10 | | | |
| 48.75 | 1.25[4] | 1,20 | 3,20 | 60 | | |
| 45 | 5[4] | 1,40 | 3,30 | 55 | 104 | (13) |
| 40 | 10[4] | 1,50 | 3,30 | 45 | 115 | (16) |

EXAMPLE 9

Example 8 was repeated with the glass powder replaced by the zinc oxide used in Example 8. Results are shown in Table 8.

TABLE 8

| Composition (w/w %) aqueous solution | | Working time (min) | Setting time (min) | Setting rate (min$^{-1}$) | Compressive strength | |
|---|---|---|---|---|---|---|
| polyacid[1] | additive | at 23° C. | at 37° C. | at 23° C. | (MPa) | (SD) |
| 50 | 0 | 2 | 4,50 | 30 | 128 | (3.4) |
| 48.75 | 1.25[2] | 2,10 | 4,40 | 35 | | |
| 47.5 | 2.5[2] | 2,40 | 4,20 | 50 | | |
| 45 | 5[2] | 3 | 5,20 | 50 | 117 | (3.7) |
| 40 | 10[2] | 3,50 | 7,40 | 20 | | |
| 48.75 | 1.25[3] | 1,40 | 4,20 | 60 | | |
| 47.5 | 2.5[3] | 2 | 5 | 50 | | |
| 45 | 5[3] | 2,10 | 5 | 35 | 120 | (6.7) |
| 40 | 10[3] | 1,40 | 5,50 | 20 | | |
| 48.75 | 1.25[4] | 2 | 4,50 | 25 | | |
| 47.5 | 2.5[4] | 2 | 3,50 | 40 | | |
| 45 | 5[4] | 2,20 | 4,30 | 50 | 124 | (5.0) |
| 40 | 10[4] | 3 | 4,30 | 45 | 127 | (4.7) |

EXAMPLE 10

The aluminosilicate powder of Example 4, to which was added 10% by weight of boron phosphate (ex BDH Ltd. and finely ground), was mixed by spatulation on a glass block at a powder:liquid ratio of 3:1 g/ml with a 40% aqueous solution of polyacrylic acid. The working time was 2 minutes 50 seconds; the setting time was 9.0 mm; and the setting rate was 22 min$^{-1}$.

EXAMPLES 11 TO 14

Example 10 was repeated with glasses of differing composition. The results are shown in Table 9.

TABLE 9

| Example No. | Glass | Working time (min) at 23° C. | Setting time (min) at 31° C. | Setting rate (min$^{-1}$) at 23° C. |
|---|---|---|---|---|
| 11 | EX. 5 | 2 mins 19 secs | 7 mins 50 secs | 23 |
| 12 | EX. 6 | 2 | <2 mins 30 secs | 37 |
| 13 | EX. 7 | 1 min 10 secs | 4 mins 10 secs | 53 |
| 14 | EX. 8 | 1 min 10 secs | 4 mins 20 secs | 27 |

EXAMPLES 15 TO 18

Example 2 was repeated but with the boron phosphate used in Examples 10 to 14 added, in amounts shown in Table 10, to the zinc oxide powder. The results are shown in Table 10.

TABLE 10

| Example No. | % weight boron phosphate added | Working time (min) at 23° C. | Setting time (min) at 37° C. | Setting rate (min) at 23° C. |
|---|---|---|---|---|
| 15 | 2.5 | 1 min 50 secs | 5 mins 0 sec | 24 |
| 16 | 5.0 | 1 min 50 secs | 5 mins 0 sec | 25 |
| 17 | 7.5 | 2 mins 0 sec | 5 mins 30 secs | 27 |
| 18 | 10 | 2 mins 10 secs | 6 mins 30 secs | 26 |

We claim:
1. A hardenable composition which comprises (i) a poly(carboxylic acid) or precursor thereof (as herein defined); (ii) a particulate ion-leachable silicate, aluminosilicate or metal oxide reactable with (i) in the presence of water to set to a hardened composition; and (iii) boron phosphate or a compound comprising at least one phosphorus-carbon covalent bond, in an amount effective in service to extend the working time of the composition.

2. A hardenable composition according to claim 1 wherein (i) comprises an acrylic acid homopolymer or copolymer acid with one or more aconitic, fumaric, itaconic, maleic, mesaconic, methacrylic, muconic or tiglic acid.

3. A hardenable composition according to claim 1 wherein (ii) comprises zinc oxide.

4. A hardenable composition according to claim 1 wherein (ii) comprises a (fluoro)aluminosilicate glass powder.

5. A hardenable composition according to claim 4 wherein the glass has a composition within the following system:
   (a) $CaO—Al_2O_3—SiO_2$;
   (b) $CaO—Al_2O_3—SiO_2—CaF_2$;
   (c) $CaF_2—Al_2O_3—SiO_2$;
   (d) $CaF_2—Al_2O_3—SiO_2—AlPO_4$; or
   (e) $CaF_2—Al_2O_3—SiO_2—AlPO_4AlF_3—Na_3AlF_6$.

6. A hardenable composition according to claim 1 wherein (iii) comprises a polybasic phosphonic acid.

7. A hardenable composition according to claim 6 wherein (iii) also comprises at least one amino group.

8. A hardenable composition according to claim 7 wherein the amino group is a tertiary amino group.

9. A hardenable composition according to claim 1 wherein (iii) is soluble in an aqueous solution of (i).

10. A hardenable composition according to claim 1 which further comprises a complexing agent soluble in an aqueous solution of (i).

11. A hardenable composition according to claim 10 wherein the complexing agent comprises a fluoride ligand.

12. A hardenable composition according to claim 10 wherein the complexing agent comprises a chelating agent.

13. A hardenable composition according to claim 12 wherein the chelating agent comprises a plurality of carboxyl groups.

14. A hardenable composition according to claim 13 wherein the chelating agent comprises aconitic, itaconic, maleic, mellitic or tricarballylic acid.

15. A hardenable composition according to claim 12 wherein the chelating agent also comprises at least one hydroxyl group.

16. A hardenable composition according to claim 15 wherein the chelating agent comprises citric, malic or tartaric acid.

17. A hardenable composition according to claim 12 wherein the chelating agent comprises a multivalent metal chelate.

18. A hardenable composition according to claim 17 wherein the chelating agent comprises a beta-diketone metal chelate or an EDTA chelate.

19. A hardenable composition according to claim 1 wherein (iii) is present in an amount of up to 20% by weight of (i).

20. A hardenable composition according to claim 1 wherein (iii) is present in an amount of up to 10% by weight of (i).

21. A hardenable composition according to any of claim 1 comprising a dry mixture of the poly(carboxylic acid) or precursor thereof (i) in particulate form; particulate ion-leachable silicate, (fluoro)aluminosilicate or metal oxide (ii); and compound (iii).

22. A hardenable composition according to claim 1 supplied as a two-component pack, one of which components may comprise an aqueous medium.

23. A hardenable composition according to claim 1 supplied as a sheet material.

24. A mixture suitable for use in preparing the hardenable composition of claim 1, which comprises compound (iii) as defined in claim 1 and (a) a complexing agent soluble in an aqueous solution of a poly(carboxylic acid) or precursor thereof (as herein defined) or (b) said poly(carboxylic acid) or said precursor or (c) said particulate component (ii) as defined in claim 1.

25. A process for preparing a hardened mass of a poly(carboxylate) cement, which comprises mixing water with components (i), (ii) and (iii) as defined in claim 1.

26. A process for preparing a hardened mass of a poly(carboxylate) cement, which comprises mixing water with components (i), (ii) and (iii) as defined in claim 1 and with a complexing agent soluble in an aqueous solution of component (i).

27. A hardened mass of a poly(carboxylate) cement prepared by the process of claim 26.

28. A hardened mass of a poly(carboxylate) cement prepared by the process of claim 25.

* * * * *